United States Patent [19]

Shibata et al.

[11] Patent Number: 5,013,475
[45] Date of Patent: May 7, 1991

[54] OPTICALLY ACTIVE ESTER COMPOUND AND LIQUID CRYSTAL COMPOSITION CONTAINING THE SAME

[75] Inventors: Toshihiro Shibata; Masaki Kimura; Norio Kurosawa, all of Urawa, Japan

[73] Assignee: Adeka Argus Chemical Co., Ltd., Tokyo, Japan

[21] Appl. No.: 427,603

[22] Filed: Oct. 27, 1989

[30] Foreign Application Priority Data

Oct. 27, 1988 [JP] Japan ................... 63-271751

[51] Int. Cl.$^5$ .................. C09K 19/34; C07C 41/00
[52] U.S. Cl. .................. 252/299.61; 252/299.01; 252/299.66; 544/298; 544/335; 560/226; 560/227; 560/255; 568/585; 568/588; 568/631
[58] Field of Search .................. 252/299.01, 299.61, 252/299.66; 544/230, 239, 295, 296, 298, 315, 357, 405, 408, 275, 276, 281, 335; 560/127, 226, 227, 255; 568/585, 631, 588

[56] References Cited

U.S. PATENT DOCUMENTS

| | | | |
|---|---|---|---|
| 4,650,600 | 3/1987 | Heppke et al. | 252/299.01 |
| 4,786,730 | 11/1988 | Shibata et al. | 544/335 |
| 4,831,143 | 5/1989 | Shibata et al. | 544/335 |
| 4,866,199 | 9/1989 | Shibata et al. | 560/65 |
| 4,886,623 | 12/1989 | Mitsuhashi et al. | 252/299.65 |
| 4,959,173 | 9/1990 | Shibata et al. | 252/299.65 |
| 4,961,875 | 10/1990 | Ohno et al. | 252/299.66 |

FOREIGN PATENT DOCUMENTS

| | | | |
|---|---|---|---|
| 279629 | 8/1988 | European Pat. Off. | 560/255 |
| 322862 | 7/1989 | European Pat. Off. | 252/299.61 |
| 63-44548 | 2/1988 | Japan | 252/299.61 |

*Primary Examiner*—John S. Maples
*Assistant Examiner*—Richard Treanor
*Attorney, Agent, or Firm*—Young & Thompson

[57] ABSTRACT

An optically active ester compound useful as a component of a ferroelectric liquid crystal composition is represented by the following formula:

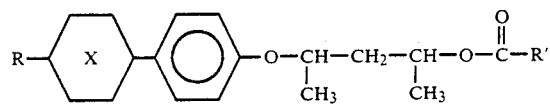

wherein R is $C_{1-18}$ alkyl or $C_{1-18}$ alkoxyl; R' is $C_{1-18}$ alkyl or $C_{1-18}$ haloalkyl; and

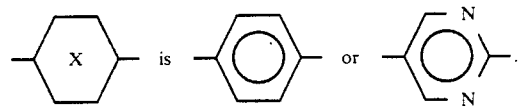

2 Claims, No Drawings

OPTICALLY ACTIVE ESTER COMPOUND AND LIQUID CRYSTAL COMPOSITION CONTAINING THE SAME

BACKGROUND OF THE INVENTION

1. Field of the Invention

The present invention relates to a novel optically active ester compound and a liquid crystal composition containing the same. More particularly, it relates to an optically active ester compound useful as a component of a ferroelectric liquid crystal composition and a ferroelectric liquid crystal composition containing the same.

2. Description of the Prior Art

Although the practical use of a liquid crystal element has started with the application thereof to the display of a watch or an electronic calculator, it is now applied to a widened field including pocket television, various displays and optoelectronic elements. Most of the liquid crystal display elements now used are of TN display type and use nematic liquid crystal materials. Since this type of display is of the photoreception type, it has disadvantages in that the speed of response is low and that the displayed images cannot be seen at some angles of vision, though it has advantages in that the eyes suffer little fatigue and that the power consumption is very low. In order to overcome these disadvantages, a display system using a ferroelectric liquid crystal has recently been proposed. Even in a display element using a ferroelectric liquid crystal, like in the case of the above TN liquid crystal display element, a ferroelectric liquid crystal must be practically used in a state mixed with several liquid crystal or non-liquid crystal compounds, i.e., as a so-called ferroelectric liquid crystal composition, in order to satisfy various characteristics.

On the basis of this idea, Japanese Patent Laid-Open No. 44548/1988 proposed the use of an optically active 2-methyl-1,3-propanediol compound as a component of a ferroelectric liquid crystal composition. However, a ferroelectric liquid crystal composition containing such a compound as a component is not sufficiently improved in the speed of response, though it is somewhat improved. Accordingly, a further improvement in the speed of response of a ferroelectric liquid crystal composition has been expected in order to put the composition to practical use.

SUMMARY OF THE INVENTION

Under these circumstances, the inventors of the present invention have intensively studied to find an optically active compound which can give a ferroelectric liquid crystal composition that is excellent in the speed of response and have found that a novel optically active ester compound represented by the following general formula (I) is very suitable for this object:

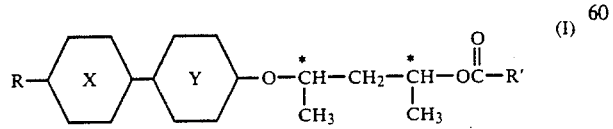

wherein R stands for a $C_{1\sim 8}$ alkyl group or a $C_{1\sim 18}$ alkoxy group; $R^1$ stands for a $C_{1\sim 18}$ organic carboxylic acid residue which may be substituted;

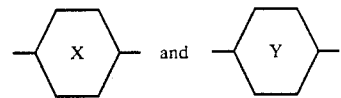

independent from each other, each stand for a benzene, pyridine, pyrimidine, pyrazine or pyridazine ring which may be substituted; and * stands for an asymmetric carbon atom.

When the optically active ester compound of the present invention represented by the above general formula (I) is used as a component of a liquid crystal composition, an SmC* phase is induced in the composition to bring about an extremely high speed of response and a large spontaneous polarization. Thus, an excellent ferroelectric liquid crystal composition can be provided.

DETAILED DESCRIPTION OF THE INVENTION

The compound represented by the general formula (I) will now be described in more detail.

The $C_{1\sim 18}$ alkyl group defined with respect to R includes methyl, ethyl, propyl, butyl, pentyl, hexyl, heptyl, octyl, nonyl, decyl, undecyl, lauryl, myristyl, palmityl and stearyl groups, while the $C_{1\sim 18}$ alkoxy group includes those derived from the above alkyl groups.

The $C_{1\sim 18}$ organic carboxylic acid residue which may be substituted, defined with respect to R', includes not only carboxylic acid residues having alkyl groups described above with respect to R, but also those having alkynyl groups such as 1-butynyl, 2-butynyl, 2-pentynyl or 3-pentynyl group; those each having an alkyl group containing an optically active or racemic methyl group, such as 1-methylbutyl, 2-methylbutyl, 4-methyloctyl, 2,6-dimethylheptyl or 2,6-dimethyl-5-heptenyl; 1-octoxypropionic acid residue; and carboxylic acid residues each having a halogen- or cyano-substituted alkyl group such as 1-chloroethyl, 1-fluoroalkyl, 1-trifluoromethylalkyl, 1-cyano-2-methylbutyl or 1-chloro-2-methylbutyl group.

Although the optically active ester compound of the present invention represented by the above general formula (I) does not always exhibit properties as a ferroelectric liquid crystal by itself, it may be mixed with other liquid crystal or non-liquid crystal compounds to give a practically usable liquid crystal composition. Representative examples of the compound to be mixed include the following compounds, though not limited to them.

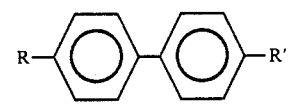

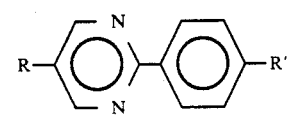

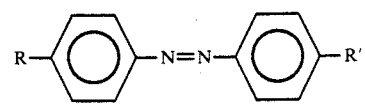

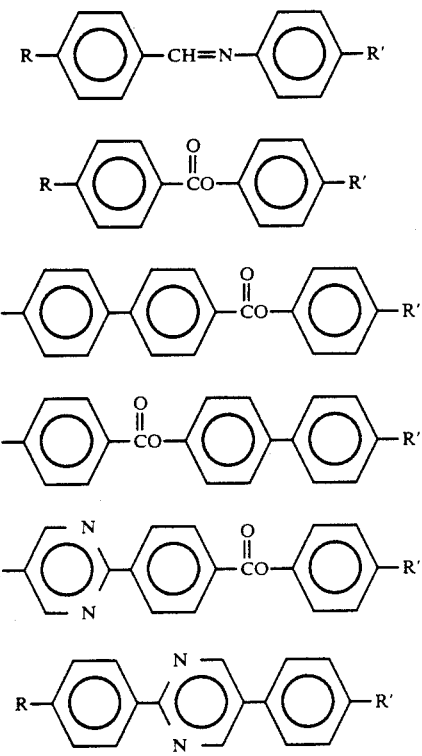

These compounds may also be used as a mixture of two or more of them with an arbitrary ratio.

According to the present invention, the optically active ester compound of the present invention is preferably used in an amount of 5 to 30 parts by weight per 100 parts by weight of a matrix liquid crystal (other liquid crystal or non-liquid crystal compound).

The present invention will now be described by referring to the following Examples, though it is not limited by them.

EXAMPLE 1 (SYNTHESIS EXAMPLE 1)

Synthesis of (1''S, 3''R)-4'-octyloxy-4-(1''-methyl-3''-butanoyloxybutyloxy)biphenyl

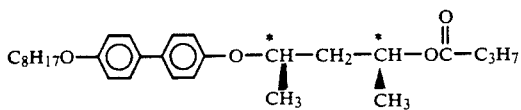

0.62 g of (R,R)-2,4-pentanediol, 1.49 g of n-octoxybiphenol, 1.57 g of triphenylphosphine and 1.04 g of diethyl azodicarboxylate were dissolved in 25 ml of ethyl ether. The obtained solution was stirred at a room temperature for 3 hours to precipitate triphenylphosphine oxide. The triphenylphosphine oxide was filtered out and the resulting filtrate was freed from the solvent. The solvent-free residue was purified by silica gel column chromatography using a n-hexane/ethyl acetate (7:3) mixture as a developing solvent to obtain 1.71 g of (1''S, 3''R)-4'-octyloxy-4-(1''-methyl-3''-hydroxybutyloxy)biphenyl as a white solid (m.p.: 69.2° to 69.9° C.).

0.38 g of the biphenyl compound prepared above, 0.11 g of butyric acid, 0.62 g of triphenylphosphine and 0.42 g of diethyl azodicarboxylate were dissolved in 10 ml of ethyl ether. The obtained solution was stirred at a room temperature for 2 hours to precipitate triphenylphosphine oxide. This triphenylphosphine oxide was filtered out and the filtrate was freed from the solvent. The solvent-free residue was purified by silica gel column chromatography using a n-hexane/ethyl acetate (95:5) mixture as a developing solvent to obtain 0.35 g of a colorless oil.

The infrared spectroscopic analysis of the oil revealed that the oil had the following characteristic absorptions, and the oil was thus identified as the objective compound:

| | | |
|---|---|---|
| 3030 cm$^{-1}$ (vw), | 2925 cm$^{-1}$ (s), | 2860 cm$^{-1}$ (m), |
| 1730 cm$^{-1}$ (s), | 1605 cm$^{-1}$ (s), | 1585 cm$^{-1}$ (vw), |
| 1495 cm$^{-1}$ (s), | 1470 cm$^{-1}$ (m), | 1380 cm$^{-1}$ (m), |
| 2495 cm$^{-1}$ (s), | 1180 cm$^{-1}$ (s), | 1105 cm$^{-1}$ (m), |
| 820 cm$^{-1}$ (s) | | |

EXAMPLE 2 (SYNTHESIS EXAMPLE 2)

Synthesis of (1''R, 3''R)-4'-octyloxy-4-(1''-methyl-3''-butanoyloxybutyloxy)biphenyl

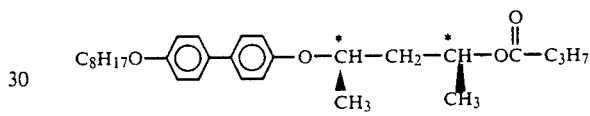

The same procedure as that described in Example 1 was repeated except that (S,S)-2,4-pentanediol was used instead of the (R,R)-2,4-pentanediol. Thus, the synthesis of the objective compound was carried out.

The infrared spectroscopic analysis of the product revealed that the product had the following characteristic absorptions and the product was thus identified as the objective compound:

| | | |
|---|---|---|
| 3030 cm$^{-1}$ (vw), | 2925 cm$^{-1}$ (s), | 2860 cm$^{-1}$ (m), |
| 1730 cm$^{-1}$ (s), | 1605 cm$^{-1}$ (s), | 1585 cm$^{-1}$ (vw), |
| 1495 cm$^{-1}$ (s), | 1470 cm$^{-1}$ (m), | 1380 cm$^{-1}$ (m), |
| 1240 cm$^{-1}$ (s), | 1180 cm$^{-1}$ (s), | 1105 cm$^{-1}$ (m), |
| 820 cm$^{-1}$ (s) | | |

EXAMPLE 3 (SYNTHESIS EXAMPLE 3)

Synthesis of (1''R, 3''R)-4'-octyloxy-4-(1''-methyl-3''-butanoyloxybutyloxy)biphenyl

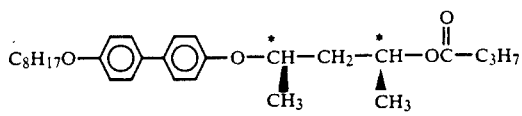

A mixture comprising 0.38 g of (1''S, 3''S)-4'-octyloxy-4-(1''-methyl-3''-hydroxybutyloxy)biphenyl, 0.79 g of butyric anhydride and 0.04 g of pyridine was reacted at 100° C. for 3 hours and the obtained reaction mixture was poured into 2 N hydrochloric acid. The obtained mixture was extracted with ethyl ether. The extract was washed with water, dried and freed from the solvent. The residue was purified by silica gel column chromatography using a n-hexane/ethyl ether (9:1)

mixture as a developing solvent to obtain 0.36 g of a colorless oil.

The infrared spectroscopic analysis of the oil revealed that the oil had the following characteristic absorptions and the oil was thus identified as the objective compound.

| 3030 cm$^{-1}$ (vw), | 2925 cm$^{-1}$ (s), | 2860 cm$^{-1}$ (m), |
| --- | --- | --- |
| 1730 cm$^{-1}$ (s), | 1605 cm$^{-1}$ (s), | 1585 cm$^{-1}$ (vw), |
| 1495 cm$^{-1}$ (s), | 1470 cm$^{-1}$ (m), | 1380 cm$^{-1}$ (m), |
| 1240 cm$^{-1}$ (s), | 1180 cm$^{-1}$ (s), | 1105 cm$^{-1}$ (m), |
| 820 cm$^{-1}$ (s) | | |

EXAMPLE 4 (SYNTHESIS EXAMPLE 4)

Synthesis of (2″R, 3″S, 1′S, 3′S)-4′-octyloxy-4-[1′-methyl-3′-(2″-chloro-3″-methyl-pentanoyloxy)-butyloxy]biphenyl

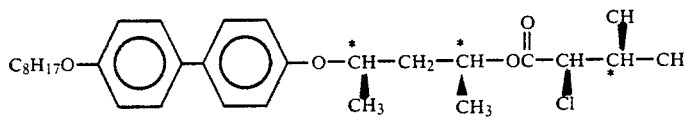

The same reaction as that described in Example 1 was carried out except that 0.18 g of (2R, 3S)-2-chloro-3-methylpentanoic acid was used instead of the butyric acid. The obtained product was purified by silica gel column chromatography using a n-hexane/ethyl acetate (95:5) mixture as a developing solvent to obtain 0.35 g of a colorless oil.

The infrared spectroscopic analysis of this oil revealed that the oil had the following characteristic absorptions and the oil was thus identified as the objective compound.

| 3030 cm$^{-1}$ (vw), | 2925 cm$^{-1}$ (s), | 2860 cm$^{-1}$ (m), |
| --- | --- | --- |
| 1740 cm$^{-1}$ (s), | 1605 cm$^{-1}$ (s), | 1580 cm$^{-1}$ (vw), |
| 1495 cm$^{-1}$ (s), | 1465 cm$^{-1}$ (m), | 1380 cm$^{-1}$ (m), |
| 1240 cm$^{-1}$ (s), | 1175 cm$^{-1}$ (s), | 1110 cm$^{-1}$ (m), |
| 820 cm$^{-1}$ (s) | | |

EXAMPLE 5 (SYNTHESIS EXAMPLE 5)

Synthesis of (1″S, 3″S)-5-decyl-2-[4′-(1″-methyl-3″-butanoyloxybutyloxy)phenyl]pyrimidine

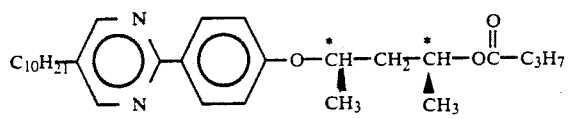

The same reaction as that described in Example 1 was carried out except that 0.40 g of (1″S, 3″R)-5-decyl-2-[4′-(1″-methyl-3″-hydroxybutyloxy)phenyl] pyrimidine was used instead of the (1″S, 3″R)-4′-octyloxy-4′(1″-methyl-3″-hydroxybutyloxy)biphenyl. The obtained product was purified by silica gel column chromatography using a n-hexane/ethyl ether (8:2) mixture as a developing solvent and distilled by the use of an Allihn condenser at 218° to 221° C./0.11 mmHg to obtain 0.20 g of a colorless oil.

The infrared spectroscopic analysis of the oil revealed that the oil had the following characteristic absorptions and the oil was thus identified as the objective compound.

| 2920 cm$^{-1}$ (s), | 2850 cm$^{-1}$ (m), | 1730 cm$^{-1}$ (s), |
| --- | --- | --- |
| 1605 cm$^{-1}$ (m), | 1585 cm$^{-1}$ (s), | 1540 cm$^{-1}$ (vw), |
| 1510 cm$^{-1}$ (w), | 1460 cm$^{-1}$ (w), | 1425 cm$^{-1}$ (s), |
| 1375 cm$^{-1}$ (w), | 1325 cm$^{-1}$ (vw), | 1300 cm$^{-1}$ (vw), |
| 1245 cm$^{-1}$ (s), | 1170 cm$^{-1}$ (s), | 1100 cm$^{-1}$ (m), |
| 940 cm$^{-1}$ (vw), | 845 cm$^{-1}$ (w) | 800 cm$^{-1}$ (m) |

EXAMPLE 6 (USAGE EXAMPLE 1)

In order to evaluate the effect of the liquid crystal composition according to the present invention, the following four compounds were mixed with each other to obtain a matrix liquid crystal composition:

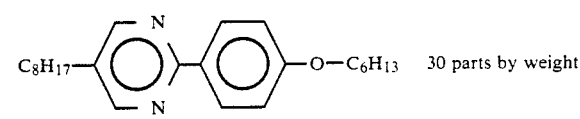  30 parts by weight

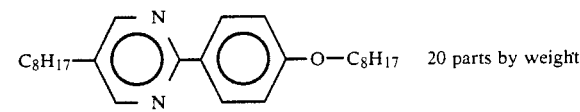  20 parts by weight

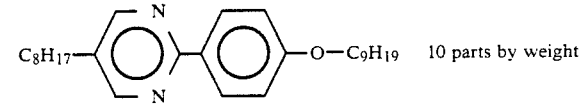  10 parts by weight

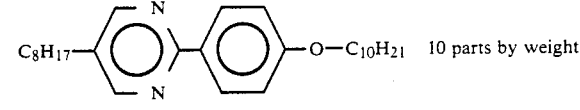  10 parts by weight

The above matrix liquid crystal composition was sandwiched between two glass plates and the phase of the composition was observed with a polarization microscope to ascertain the following phase transition:

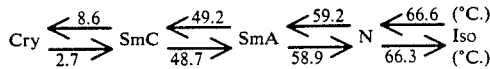

90% by weight of the matrix liquid crystal composition was mixed with 10% by weight of an optically active ester compound of the present invention listed in Table 1 to prepared a liquid crystal composition. The phase transition temperatures of the composition were determined by the use of a polarization microscope in a similar manner to that described above. Further, the liquid crystal composition was injected into a transparent electrode cell of 2 μm thick glass oriented by rubbing and heated to 120° C. to obtain an isotropic liquid. The liquid crystal cell was gradually cooled and examined for the speed of response by applying a rectangular wave of ±15 V and 1 Hz thereto under crossed nicols. Further, the spontaneous polarization was determined by the triangular wave method. The results are shown in Table 1.

It can be understood from the results shown in Table 1 that the optically active ester compound of the present invention induces an SmC* phase to bring about an extremely short response time and a large spontaneous polarization even when it is added to a matrix liquid crystal composition only in an amount of 10%.

EXAMPLE 7 (USAGE EXAMPLE 2)

A matrix liquid crystal composition comprising the following components was prepared in a similar manner to that of Example 6:

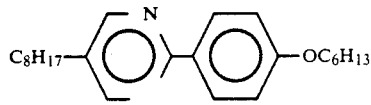  20 parts by weight

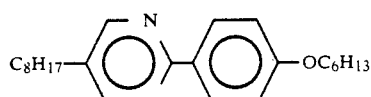  20 parts by weight

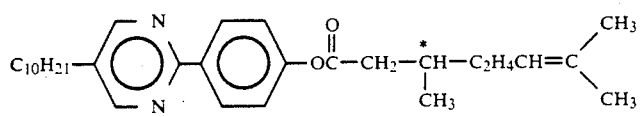  16 parts by weight

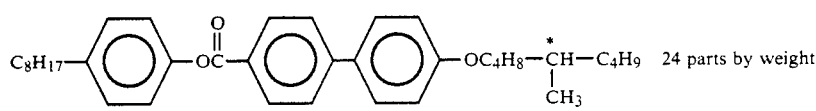  24 parts by weight

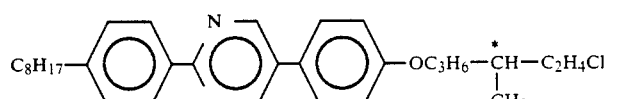  10 parts by weight

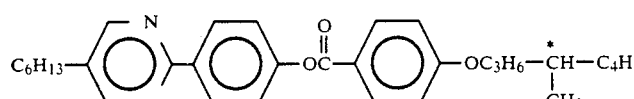  10 parts by weight

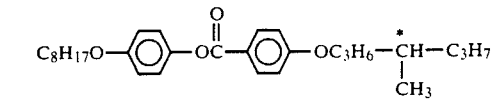  30 parts by weight

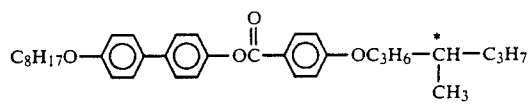  40 parts by weight

90% by weight of the matrix liquid crystal composition prepared above was mixed with 10% by weight of an optically active ester compound of the present invention:

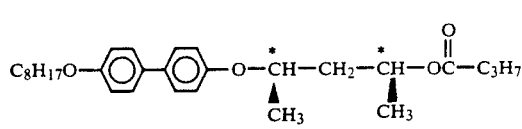

to obtain a liquid crystal composition. This liquid crystal composition was examined for phase transition temperatures, speed of response and spontaneous polarization. The results are shown in Table 2.

EXAMPLE 8 (USAGE EXAMPLE 3)

A matrix liquid crystal composition comprising the following components was prepared in a similar manner to that of Example 6:

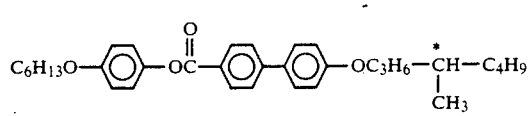 10 parts by weight 20 parts by weight

90% by weight of the matrix liquid crystal composition prepared above was mixed with 10% by weight of an optically active ester compound of the present invention listed in Table 3 to obtain a liquid crystal composition. This liquid crystal composition was examined for phase transition temperatures, response time and spontaneous polarization. The results are shown in Table 3.

As shown in the foregoing Examples, when the optically active ester compound of the present invention is used as a component of a liquid crystal composition, an SmC* phase is induced in the composition, so that the composition exhibits an extremely high speed of response and a large spontaneous polarization. Thus the present invention can provide an excellent ferroelectric liquid crystal composition.

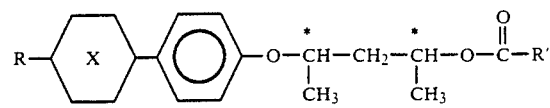

TABLE 1

| Compound of the present invention | SmC* | SmA | N* | Iso | τ (μsec) Tc − T = 10 | Ps (nC/cm²) Tc − T = 10 |
|---|---|---|---|---|---|---|
| $H_{21}C_{10}$—[pyrazine]—[phenyl]—OCHCH$_2$CHOOCC$_3$H$_7$ (CH$_3$, CH$_3$) | · 25.9 · | 50.5 · | 58.1 · | | 330 | −2.9 |
| $H_{17}C_8O$—[phenyl]—[phenyl]—OCHCH$_2$CHOOCC$_3$H$_7$ (CH$_3$, CH$_3$) | · 32.4 · | 46.2 · | 57.3 · | | 320 | −4.4 |
| $H_{17}C_8O$—[phenyl]—[phenyl]—OCHCH$_2$CHOOCC$_3$H$_7$ (CH$_3$, CH$_3$) | · 32.1 · | 46.4 · | 57.0 · | | 320 | +4.4 |
| $H_{17}C_8O$—[phenyl]—[phenyl]—OCHCH$_2$CHOOCC$_3$H$_7$ (CH$_3$, CH$_3$) | · 33.8 · | 48.5 · | 57.0 · | | 700 | −0.5 |
| $H_{17}C_8O$—[phenyl]—[phenyl]—OCHCH$_2$CHOOCCH—CHC$_2$H$_5$ (CH$_3$, CH$_3$, Cl, CH$_3$) | · 27.5 · | 44.5 · | 56.3 · | | 380 | −3.9 |

TABLE 2

| Compound of the present invention | SmC* | SmA | N* | Iso | τ (μsec) Tc − T = 10 | Ps (nC/cm²) Tc − T = 10 |
|---|---|---|---|---|---|---|
| Matrix liquid crystal composition — not used | · 59 · | 73 · | 84 · | | 330 | +2.2 |
| Liquid crystal composition $H_{17}C_8O$—[phenyl]—[phenyl]—OCHCH$_2$CHOCC$_3$H$_7$ (CH$_3$, CH$_3$) | · 45 · | 70 · | — · | | 280 | +8.8 |
| Matrix liquid crystal composition — not used | · 76.5 · | 87.9 · | 100.5 · | | 530 | ≈0 |
| Liquid crystal composition $H_{17}C_8O$—[phenyl]—[phenyl]—OCHCH$_2$CHOCC$_3$H$_7$ (CH$_3$, CH$_3$) | · 63.7 · | 72.0 · | — · | | 380 | +3.1 |

What is claimed is:

1. An optically active ester compound of the formula: wherein R is $C_{1-18}$ alkyl or $C_{1-18}$ alkoxy; R' is $C_{1-18}$ alkyl or $C_{1-18}$ haloalkyl; and

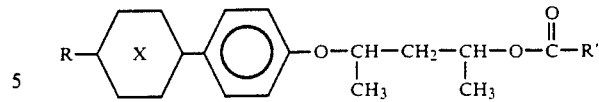
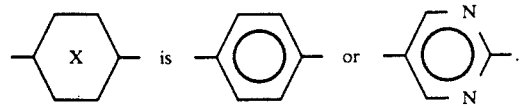
2. A ferroelectric liquid crystal composition containing an optically active ester compound of the formula:
wherein R is $C_{1-18}$ alkyl or $C_{1-18}$ alkoxy; R' is $C_{1-18}$ alkyl or $C_{1-18}$ haloalkyl; and
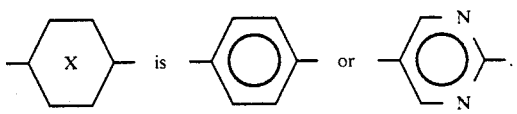
* * * * *